United States Patent [19]

Vellekamp et al.

[11] Patent Number: 5,710,251
[45] Date of Patent: Jan. 20, 1998

[54] PURIFICATION OF BACTERIALLY EXPRESSED HUMAN INTERLEUKIN-10

[75] Inventors: Gary Vellekamp, Glen Ridge; Susan Cannon-Carlson, Wayne; John Tang, Livingston, all of N.J.

[73] Assignee: Schering Corporation, Kenilworth, N.J.

[21] Appl. No.: 495,558

[22] PCT Filed: Mar. 3, 1994

[86] PCT No.: PCT/US94/01909

§ 371 Date: Dec. 18, 1995

§ 102(e) Date: Dec. 18, 1995

[87] PCT Pub. No.: WO94/20525

PCT Pub. Date: Sep. 15, 1994

Related U.S. Application Data

[63] Continuation-in-part of Ser. No. 26,942, Mar. 5, 1993, Pat. No. 5,328,989.

[51] Int. Cl.$^6$ .................... C07K 14/54; C07K 1/18; C07K 1/22; C07K 1/36
[52] U.S. Cl. .............. 530/351; 435/69.52; 435/70.4; 530/415; 530/416
[58] Field of Search ............... 530/417, 415, 530/416, 351, 412; 435/69.52, 70.1, 70.3, 70.4

[56] References Cited

U.S. PATENT DOCUMENTS

| | | | |
|---|---|---|---|
| 4,751,078 | 6/1988 | Nagabhushan et al. | 530/351 |
| 4,855,238 | 8/1989 | Gray et al. | 435/243 |
| 4,929,700 | 5/1990 | Halenbeck et al. | 530/351 |
| 5,055,555 | 10/1991 | Sassenfeld | 530/351 |
| 5,227,302 | 7/1993 | Heldin et al. | 435/240.2 |
| 5,231,012 | 7/1993 | Mosmann et al. | 435/69.52 |
| 5,328,989 | 7/1994 | Vellekamp et al. | 530/351 |
| 5,368,854 | 11/1994 | Rennick | 424/85.2 |

FOREIGN PATENT DOCUMENTS

| | | |
|---|---|---|
| 0 061 139 | 9/1982 | European Pat. Off. |
| WO 91/00349 | 1/1991 | WIPO |

OTHER PUBLICATIONS

Hisatsune T., et al, Lym. & Cyto. Res., vol. 11, No. 2:87–93 (1992).
Ingley, E. et al, Eur. J.Biochem, vol. 196:623–629(1991).
Mosman, T., et al, J. Immun. vol. 145:2938–2945 (1990).
Fiorentino, D., et al, J. Exp.Med., vol. 170:2081–2095 (1989).

*Primary Examiner*—David Guzo
*Assistant Examiner*—Nancy T. Degen
*Attorney, Agent, or Firm*—Jaye P. McLaughlin; Norman C. Dulak

[57] ABSTRACT

Disclosed is a method for purifying Interleukin-10 (IL-10). The method is comprised of subjecting an IL-10 containing solution to cation exchange chromatography, anion exchange chromatography, hydroxyapatite chromatography, and gel filtration chromatography. The present invention is also comprised of a process for separating different IL-10 dimers present in a protein fraction from each other by subjecting the protein fraction to hydroxyapatite chromatography. The present invention is also comprised of a process for separating variants of a protein differing in an N-terminal amino acid sequence present in a protein fraction from each other by subjecting the protein fraction to hydroxyapatite chromatography.

9 Claims, No Drawings

PURIFICATION OF BACTERIALLY EXPRESSED HUMAN INTERLEUKIN-10

The present application is the United States national application corresponding to International Application No. PCT/US94/01909, filed Mar. 3, 1994 designating the United States, which PCT application is in turn a continuation-in-part of U.S. application Ser. No. 08/026,942, filed Mar. 5, 1993, now U.S. Pat. No. 5,328,989 the benefit of which applications are claimed pursuant to the provisions of 35 U.S.C. 120, 363, and 365 (C).

BACKGROUND OF THE INVENTION

Interleukin-10 (IL-10), a recently discovered lymphokine, was originally described as an inhibitor of interferon-γ synthesis and is postulated as a major mediator of the humoral class of immune response [Fiorentino, D. F., et al., *J. Exp. Med.* 170:2081 (1989) and Moore et al., K. W., et al., *Science* 248:1230–1234 (1990)]. Two classes of often mutually exclusive immune responses are the humoral (antibody-mediated) and the delayed-type hypersensitivity.

It is postulated that these two differing immune responses may arise from two types of helper T-cell clones, namely Th1 and Th2 helper T-cells, which demonstrate distinct cytokine secretion patterns [Moore supra; Vieira, P. et al., *Proc. Nat. Acad. Sci. USA* Vol. 88:1172 (1991)]. Mouse Th1 cell clones secrete interferon-γ, and IL-2 and preferentially induce the delayed-type hypersensitivity response while Th-2 cell clones secrete IL-4, IL-5 and IL-10 and provide support for the humoral responses [Fiorentino et at., supra]. The contrast in immune response could result because interferon-γ secreted by the Th1 cell clones inhibits Th2 clone proliferation in vitro, while IL-10 secreted by the Th2 cell clones inhibit cytokine secretion by the Th1 cell clones [Fiorentino et al., supra and Moore et al., supra]. Thus the two T-helper cell types may be mutually inhibitory and may provide the underpinning for the two dissimilar immune responses.

IL-10 has been cloned and sequenced from both murine and human T cells [Moore et al., supra; Vieira et al., supra]. Both sequences contain an open reading frame encoding a polypeptide of 178 amino acids with an N-terminal hydrophobic leader sequence of 18 amino acids, and have an amino acid sequence homology of 73%.

Biologically active IL-10 is a dimer as determined by analytical gel filtration. Generally, the dimer is non-covalently bonded based upon its migration as a monomer on non-reducing sodium dodecyl sulfate-polyacrylamide gel electrophoresis. Recombinant human IL-10 can be expressed both by prokaryotic and eukaryotic expression systems.

N-terminal analysis of recombinant human IL-10 produced in a eukaryotic expression system indicates that a small percentage of IL-10 polypeptides have the first two N-terminal amino acid residues missing. This truncated polypeptide is referred to as the Δ2 IL-10 polypeptide, or simply Δ2. The full-length chain is therefore referred to as Δ0, indicating that no amino acid has been deleted. Accordingly, biologically active, eukaryotically expressed IL-10 can appear as three different dimers. The first biologically active dimer and the major form is Δ0:Δ0, a homodimer in which both polypeptides of the dimer have the full-length chain of amino acids. The second IL-10 dimer is Δ0:Δ2, a heterodimer in which one of the polypeptide chains has the full-length chain of amino acids and the second chain, Δ2, has the first two N-terminal amino acids missing. The third IL-10 dimer is Δ2:Δ2, a homodimer in which both polypeptide chains of the dimer have the initial two N-terminal amino acid residues missing. Thus, there is a need for a process to purify IL-10, and in particular there is a need for a process which separates the different dimers of IL-10 from each other.

IL-10 contained in inclusion bodies expressed by a prokaryotic expression system must be, denatured, refolded, and purified from contaminants including host proteins, modified variants of IL-10 and heterodimers of those variants. Furthermore, in a prokaryotic system, the IL-10 monomer can be acetylated at one or more of the lysine residues. If an acetylated monomer binds to another acetylated monomer then an acetylated homodimer is produced. If however, a non-acetylated monomer binds to another non-acetylated monomer then a non-acetylated homodimer is produced. If an acetylated monomer binds to a non-acetylated monomer then a heterodimer is produced. Furthermore, IL-10 is normally produced as a non-covalently bonded homodimer. However, during denaturing of the inclusion bodies, and refolding of the IL-10 a covalently bonded homodimer can be produced, i.e. one which migrates as a dimer on non-reducing SDS-PAGE but as a monomer under reducing conditions. This is probably caused by one or more intermolecular disulfide bonds which are formed between the two monomers. Thus, there is a need to purify IL-10 from host protein contaminants and to obtain essentially pure non-covalently bonded dimeric IL-10 free of the acetylated homodimer, heterodimer variants and covalent dimers.

In light of its role as a potential immune response mediator and its activity as an inhibitor of interferon-γ synthesis, IL-10 may have clinical utility in autoimmune diseases or transplant rejection. However, in a clinical setting it is highly desirable that the IL-10 be in a highly pure state, substantially free of other contaminating host and medium proteins or polypeptides. Thus, there is a need for a process to purify IL-10 which accomplishes these objectives.

SUMMARY OF THE INVENTION

The present invention fills this need by providing a process for purifying IL-10 contained within a solution comprising:

(a) subjecting the solution containing IL-10 to cation exchange chromatography thereby obtaining fractions containing IL-10;

(b) subjecting the IL-10-containing fractions from step (a) to anion exchange chromatography thereby obtaining fractions containing IL-10;

(c) subjecting the IL-10-containing fractions from step (b) to hydroxyapatite chromatography thereby obtaining fractions containing a single isolated dimer of IL-10; and (d) subjecting the IL-10-containing fractions from step (c) to gel-filtration chromatography thereby obtaining IL-10 containing fractions free of high and low molecular weight impurities.

The purification process of IL-10 can be used for IL-10 expressed in bacterial or eukaryotic expression systems.

The present invention further provides a method for separating different IL-10 dimers contained within a protein fraction containing a mixture of dimers comprising subjecting the fraction to hydroxyapatite chromatography under conditions in which the dimers separate from each other.

The present invention further provides a method for separating different dimers of a protein contained within a protein fraction wherein the different dimers have different N-terminal amino acid sequences comprising subjecting the protein fraction to hydroxyapatite chromatography under conditions wherein the different dimers of the protein are separated from each other.

The present invention further provides a method for separating variants of a protein contained within a protein fraction wherein the variants of the protein have different N-terminal amino acid sequences comprising subjecting the protein fraction to hydroxyapatite chromatography under conditions wherein the variants of the protein are separated from each other.

The present invention still further provides a method for separating non-acetylated homodimers of IL-10 from acetylated homodimers and from acetylated heterodimers of IL-10 contained within a solution comprising subjecting the solution to anion exchange chromatography under conditions in which the non-acetylated homodimer is separated from the acetylated dimers of IL-10.

DESCRIPTION OF THE INVENTION

All references cited herein are hereby incorporated in their entirety by reference.

As used herein, "interleukin-10" or "IL-10" can be either human IL-10 (h IL-10) or murine IL-10. Human IL-10 is defined as a protein which (a) has an amino acid sequence substantially identical to a known sequence of mature (i.e., lacking a secretory leader sequence) hIL-10 as disclosed in U.S. patent application Ser. No. 07/917,806, filed Jul. 20, 1992, now U.S. Pat. No. 5,231,012, which corresponds to International Application No. PCT/US90/03554, Publication No. WO 91/00349, and (b) has biological activity that is common to native hIL-10.

IL-10 can be obtained from culture media of activated T-cells capable of secreting the protein. Preferentially, however, it is obtained by recombinant techniques using isolated nucleic acids encoding for the IL-10 polypeptide. General methods of molecular biology are described, e.g., by Sambrook, et al., *Molecular Cloning, A Laboratory Manual*, Cold Spring Harbor Publish., Cold Spring Harbor, N.Y., 2d ed. 1989 and by Ausubel et al., (eds.) *Current Protocols in Molecular Biology*, Green/Wiley, New York (1987 and periodic supplements). The appropriate sequences can be obtained from either genomic or cDNA libraries. Polymerase chain reaction (PCR) techniques can be used. See, e.g., *PCR Protocols: A Guide to Methods and Applications*, 1990, Innis et al., (Ed.), Academic Press, New York, N.Y.

Libraries are constructed from nucleic acid extracted from appropriate cells. See, for example, International Application Publication No. WO 91/00349, which discloses recombinant methods to make IL-10. Useful gene sequences can be found, e.g., in various sequence data bases, e.g., Gen Bank and EMBL for nucleic acid, and PIR and Swiss-Prot for protein, c/o Intelligenetics, Mountain View, Calif., or the Genetics Computer Group, University of Wisconsin Biotechnology Center, Madison, Wis., which are incorporated herein by reference.

Clones comprising sequences that encode human IL-10 (hIL-10) have been deposited with the American Type Culture Collection (ATCC), Rockville, Md., under Accession Numbers 68191 and 68192. Identification of other clones harboring the sequences encoding IL-10 is performed by either nucleic acid hybridization or immunological detection of the encoded protein, if an expression vector is used. Oligonucleotide probes based on the deposited sequences are disclosed in International Application Publication No. WO 91/00349. Oligonucleotide probes useful for identification of the sequences can also be prepared from conserved regions of related genes in other species. Alternatively, degenerate probes based on the amino acid sequence of IL-10 can be used.

Various expression vectors can be used to express DNA encoding IL-10. Conventional vectors used for expression of recombinant proteins used for expression of recombinant proteins in prokaryotic or eukaryotic cells may be used. Preferred vectors include the pcD vectors described by Okayama et al., *Mol. Cell. Bio.* Vol. 3:280–289 (1983); and Takebe et al., *Mol. Cell. Biol.* Vol. 8:466–472 (1988). Other SV40-based mammalian expression vectors include those disclosed in Kaufman et al., *Mol. Cell. Biol.* Vol. 2:1304–1319 (1982) and U.S. Pat. No. 4,675,285. These SV40-based vectors are particularly useful in COS7 monkey cells (ATCC No. CRL 1651), as well as in other mammalian cells such as mouse L cells and CHO cells.

Standard transfection methods can be used to produce eukaryotic cell lines which express large quantities of the polypeptide. The process of the present invention is a process to purify IL-10 expressed by eukaryotic cells from a cell supernatant into which the protein was expressed. Eukaryotic cell lines include mammalian, yeast and insect cell lines. Exemplary mammalian cell lines include COS-7 cells, mouse L cells and Chinese Hamster Ovary (CHO) cells. See Sambrook et al., supra and Ausubel et al., supra.

Furthermore, the method of the present invention provides for a method to purify IL-10 produced by genetically transformed bacteria, particularly *E. coli*. As used herein, the term "transformed bacteria" means bacteria that have been genetically engineered to produce a mammalian protein. Such genetic engineering usually entails the introduction of an expression vector into a bacterium. The expression vector is capable of autonomous replication and protein expression relative to genes in the bacterial genome. Construction of bacterial expression is well known in the art, provided the nucleotide sequence encoding a desired protein is known or otherwise available. For example, DeBoer in U.S. Pat. No. 4,551,433 discloses promoters for use in bacterial expression vectors; Goeddel et al. in U.S. Pat. No. 4,601,980 and Riggs, in U.S. Pat. No. 4,431,739 disclose the production of mammalian proteins by *E. coli* expression systems; and Riggs supra, Ferretti et al. *Proc. Natl. Acad. Sci.* 83:599 (1986), Sproat et al., *Nucleic Acid Research* 13:2959 (1985) and Mullenbach et al., *J. Biol. Chem* 261:719 (1986) disclose how to construct synthetic genes for expression in bacteria. Many bacterial expression vectors are available commercially and through the American Type Culture Collection (ATCC), Rockville, Md.

The method of the present invention comprises the sequential application of cation-exchange, anion-exchange, hydroxyapatite and gel-filtration chromatography. To achieve high purity and maximal yield, each of the four chromatographic steps were selected and optimized in regards to pH, conductivity, buffer composition, flow rates and column dimensions. The analytic procedures utilized to determine this optimization of purity and yield were Western blots, sodium dodecyl sulfate- polyacrylamide gel electrophoresis (SDS-PAGE) Laemmli, U. K., *Nature* 227:680 (1970), Enzyme-Linked Immunoadsorbant Assay (ELISA) values, UV absorbance at 280 and 260 nm and protein concentration determinations [(Bradford, M., *Anal. Biochem.*, 72:248 (1976)].

Furthermore, the order of chromatographic steps were optimized for efficient and rapid large-scale processing as well as product purity and yield. This includes 1) product concentration during the first step (cation exchange) to reduce volume handling; 2) a flow-through mode for the second step (anion exchange) such that the product of this fast step can immediately be loaded on the next column without extra processing; 3) the removal of almost all contaminating proteins during the first two steps so that there is no interference by these other proteins with the resolution of the IL-10 forms on the third column (hydroxyapatite) and 4) besides separation of trace contaminants of differing molecular weights and IL-10 monomer, the buffer exchange of the gel filtration chromatography allows the final product IL-10 to be obtained in a buffer desired for further pharmaceutical formulation.

The cation exchange chromatography step is used first because IL-10 adsorbs well to a cation exchange resin. Any cationic exchange group can be used such as carboxymethyl, sulfopropyl and sulfonate. The cationic exchange group can be attached to any solid-phase support including but not limited to cellulose, dextrans, agarose and polystyrene. The preferred cation exchange group is sulfonate attached to an agarose packing support matrix, such an S-SEPHAROSE Fast Flow® from (Pharmacia, Piscataway, N.J.). The equilibrating buffer should be at a pH lower than 7.8, the pI of IL-10, and preferably about 6.5 for S-SEPHAROSE, in order to create sufficient positive charges on the IL-10 protein. This creates good adhesion of the IL-10 protein to the cationic exchange group.

If the IL-10 is produced by a mammalian cell culture expression system, conditions are optimized such that 80–90% of contaminant proteins, and especially serum albumin, the major contaminant protein, are not bound. The amount of protein that is to be loaded can be determined experimentally based upon information provided by the manufacturer. Using a 5×28 cm S-SEPHAROSE® Fast Flow column, approximately 100 mg protein/ml of bed volume can be applied at a flow rate of 1.1 cm/min. After the supernatant is loaded, the column is developed with either a step or linear gradient salt solution, preferably a 70–300 mM NaCl linear gradient for an S-SEPHAROSE® column. IL-10 elutes at a concentration of about 150 mM NaCl at a distinct peak of $A_{280}$ at approximately 17 mS. Ideally IL-10 containing fractions are then concentrated and diafiltered by, for example, using a PELLICON®, 10K membrane.

If IL-10 is produced in inclusion bodies in a bacterial expression system, the IL-10 is generally denatured and then refolded. A solution containing the refolded IL-10 is then applied to the cation exchange resin as described above. Conditions are optimized such that 80–90% of contaminant proteins are not bound. The amount of protein that is to be loaded can be determined experimentally based upon information provided by the manufacturer. Using a 12×36 cm S-SEPHAROSE® Fast Flow column, approximately 15 mg protein/ml of bed volume can be applied at a flow rate of 1 cm/min. After the supernatant is loaded, the column is developed with either a step or linear gradient salt solution, preferably a 65–400 mM NaCl linear gradient for an S-SEPHAROSE® column. IL-10 elutes at a concentration of about 150 mM NaCl at a distinct peak of $A_{280}$ at approximately 17 mS. Ideally IL-10 containing fractions are then concentrated and diafiltered by, for example, using a PELLICON®, 10K membrane.

The IL-10-containing fractions from the cation exchange chromatography are subjected to anion exchange chromatography which substantially removes the remaining host or cell culture protein contaminants. Any anionic exchange group can be used. Examples are quaternary aminoethyl, mixed amine or other intermediate base or weak base exchange groups. Quaternary aminoethyl is a preferred anion exchange group. The quaternary aminoethyl group may be attached to a dextran, cellulose, agarose or acrylic support matrix. Preferably the support is agarose. An ideal QAE agarose anion exchange resin is Q-SEPHAROSE® (Pharmacia, Piscataway, N.J.).

IL-10 produced by a mammalian cell culture system does not adsorb to a QAE anion exchange resin at the optimal pH of 8.0–8.3. Thus, IL-10 passes through a QAE column while most contaminating proteins are adsorbed if the mg protein/ml bed volume is below 4.

Acetylation of IL-10 contained within a fraction can be determined by first separating the variants of IL-10 by reverse-phase high performance liquid chromatography (HPLC). Mass spectometry of the intact protein or trypsin-digested fragments can then be performed. Mass spectrum analysis would then indicate an increase in mass of the IL-10 or fragment thereof equivalent to the mass of an acetyl group if the IL-10 or fragment is acetylated. In addition, N-terminal sequence analysis of trypsin-digest fragments demonstrates a peak which matches an acetylated-lysine standard if the IL-10 is acetylated. The non-acetylated IL-10 produced in a prokaryotic system adsorbs weakly to the anion exchange resin as it passes through when the solution containing the protein is at a conductivity of 1.0–1.5 and pH 8.7. The acetylated dimers and contaminant host proteins adsorb more tightly to the column.

The IL-10-containing protein fractions obtained from the anion exchange column are subjected to hydroxyapatite chromatography in order to separate the different dimeric forms of IL-10 present in the fractions. This can be done by a fast flow method in which the anion exchange column is placed directly above the hydroxyapatite column so that the fractions from the anion exchange column are immediately loaded onto the hydroxyapatite column as they come off of the anion exchange column.

If the IL-10 is produced in a mammalian cell culture system, the hydroxyapatite column is equilibrated with a standard salt solution at a pH of about 8.1. A suitable buffer for this purpose is comprised of 20 mM Tris-Cl, and 20 mM NaCl, pH 8.1. The IL-10 containing fractions are loaded onto the hydroxyapatite column and eluted preferably with a 20 bed volume linear gradient of a 150 mM potassium phosphate buffer at about a pH of 8.0. The elution is started with about a 6% concentration of the $KPO_4$ buffer and increases gradually until a concentration of about 75% is reached. $NaPO_4$ can also be used at the same concentration levels. The Δ0:Δ0 IL-10 dimer elutes off at about a 20–25% concentration of the 150 mM $KPO_4$ buffer. The other two dimers elute off at about 30–35% of the 150 mM $KPO_4$ buffer. Δ0:Δ2 can then be separated from Δ2:Δ2 preferably by doubling the length of the column and applying and reapplying the resultant fractions until the Δ0:Δ2 and the Δ2:Δ2 come out in separate fractions. Using hydroxyapatite chromatography, different IL-10 dimers present together in IL-10-containing fractions can be separated from each other. The fact that the different dimers have indeed been separated can be determined by N-terminal amino acid residue sequence analysis.

If the IL-10 is produced in a prokaryotic expression system, the truncated dimers are rare. However, non-covalently bonded IL-10 dimers must be separated from covalently bonded IL-10 dimers. This is done by hydroxyapatite chromatography. The hydroxyapatite column is equilibrated with a standard salt solution at a pH of about 7.4. A suitable buffer for this purpose is comprised of 20 mM Tris-Cl, and 20 mM NaCl, pH 7.4. The IL-10 containing fractions are loaded onto the hydroxyapatite column and eluted preferably with a 20 bed volume linear gradient of a 150 mM sodium phosphate buffer, pH 7.4. The elution is started with about a 5% concentration of the NaPO$_4$ buffer and increases gradually until a concentration of about 100% is reached. KPO$_4$ can also be used at the same concentration levels. The non-covalently bonded dimer elutes off first at 7–10 mS, and the covalently bonded dimer peaks at about 12 mS.

The isolated IL-10-dimer-containing fractions obtained from the hydroxyapatite column are then subjected to gel filtration. Gel filtration is used to separate high and low molecular weight impurities including IL-10 monomer. Two particularly useful gels are SEPHACRYL S-200 HR® which has a fractionation range of 5 kDa to about 250 kDa for proteins, and SEPHACRYL S-100 ®, which has a fractionation range of 1 to 100 kDa for proteins. Other gels which have fractionation ranges from about 1 kDa to 600 kDa for proteins may also be used.

Variant forms of a protein differing in the N-terminal amino acid sequence can be separated using hydroxyapatite chromatography. A protein, monomeric or oligomeric, may be purified but still retain heterogeneity due to variants missing one or more N-terminal amino acids. These variants may be separated by hydroxyapatite chromatography. In order to effect these separations a number of experimental variables are examined. First is the phosphate concentration necessary to elute, and the gradient of the phosphate concentration. Secondary variables to be examined are the column length, protein loading, pH, net conductivity and low levels of divalent cations. Rechromatography under somewhat altered conditions is likely to improve the yield and purity of the variant forms.

The following examples are included to illustrate but not limit the present invention.

EXAMPLE 1

Purification of Human IL-10 from CHO—Cell Line Culture Medium

Chinese Hamster Ovary (CHO) cells were transfected with a vector containing the IL-10 gene and were grown in Iscove's Modified Dulbecco's Medium (IMDM) a basal medium containing salts, buffers, vitamins, amino acids, and glucose (Sigma, St. Louis, Mo.) supplemented with 5% NUSERUM V® a medium supplement containing 25% newborn calf serum, hormones growth factors and other nutrients (Collaborative Research) and HBCHO® a serum-free supplement containing bovine serum albumin, insulin, transferrin, fetuin, fatty acids, ethanolamine, and selenium (Irvine Scientific). The transfected CHO cells were grown in the cell medium at 37° C. at a pH of 7.2. After five days of growth, a total of 177 liters of the cell culture supernatant liquid was drawn off, subjected to crossflow microfiltration and concentrated to about 17.6 liters by ultrafiltration. The CHO—cell culture supernatant was then diafiltered with 20 mM MES (2-[N-Morpholino]ethanesulfonic acid), 65 mM NaCl, pH 4. The resultant supernatant liquid was then subjected to the following chromatographic procedures, all of which were performed at 4° C.

Cation-Exchange Chromatography

The concentrated, diafiltered CHO-cell supernatant concentrate was loaded on a 5×28 cm S-SEPHAROSE ® Fast Flow column equilibrated with 20 mM MES, 70 mM NaCl pH 6.5. Approximately 100 mg protein/ml of bed volume was applied at a flow rate of 1.1 cm/min. The column was washed with 8.5 bed volumes of equilibration buffer. This was followed by elution with a 13 bed volume, 70–300 mM NaCl gradient at a reduced flow rate of 0.6 cm/min. The hIL-10 eluted at a distinct peak of $A_{280}$ at approximately 17 mS which corresponded to about 150 mM NaCl and it was the major protein eluted at 16–20 mS. The fractions containing hIL-10 were concentrated and diafiltered (PELLICON ®, 10K membrane) with Buffer A, which was comprised of 20 mM Tris-Cl, 20 mM NaCl, pH 8.1.

Cation-exchange chromatography utilizing S-SEPHAROSE ®, produced good adsorption and was therefore chosen as the first purification step. Using the conditions described above, 80–90% of the contaminant protein was not bound. Although hIL-10 was 1% of the initial protein, it was the major protein eluted at 16–20 mS and was purified 50-fold. See Table 1 below. Optimal conditions of pH, conductivity, flow rates, and column dimensions were determined by evaluating UV absorbance at 280 and 260 nm, protein concentration, ELISA values, SDS-PAGE, and Western blot results of numerous chromatographies.

Anion-Exchange Chromatography

The concentrated, diafiltered, IL-10-containing fractions obtained from the cation-exchange chromatography step were loaded on a 5×13 cm Q-SEPHAROSE® Fast Flow column equilibrated with Buffer A. The protein loading was approximately 3.5 mg/ml bed volume at 0.5 cm/min. The column was then washed with the Buffer A until the absorbance at $A_{280}$ was minimal. The protein which did not adsorb to the Q-SEPHAROSE® contained the hIL-10 and was pooled for direct loading onto hydroxyapatite.

Human IL-10 had little affinity for various anion exchange columns, showing minimal binding at pHs up to 8.1, and conductivities down to 4mS. This allowed Q-SEPHAROSE® chromatography in the flow-through mode where hIL-10 passed directly through the column, while most contaminating proteins were adsorbed if the mg protein/ml bed volume was kept below 4. Since there is no buffer adjustment of the Q-SEPHAROSE® pool prior to hydroxyapatite chromatography, the two columns can be connected in tandem so that the effluent of the Q-SEPHAROSE® column is loaded directly on the hydroxyapatite column.

Hydroxyapatite Chromatography

The IL-10 containing fractions obtained from the Q-SEPHAROSE® column were loaded on a 2.6×26 cm hydroxyapatite column and equilibrated with Buffer A in order to separate the IL-10 dimers which were present in the fractions. The hydroxyapatite which was used was a ceramic hydroxyapatite from Pentax and distributed by American International Chemical Inc. Ceramic hydroxyapatite is formed by heating, i.e., sintering, the hydroxyapatite crystals into beads. Standard, i.e., non-sintered, hydroxyapatite (Biorad) is also acceptable. The protein loading was at approximately 2.5 mg/ml bed volume at a flow rate of 0.6 cm/min. The column was washed with 5 bed volumes of a mixture of 94% Buffer A and 6% Buffer B. Buffer B was comprised of 150 mM KPO$_4$, pH 8.0. The IL-10 was eluted with a linear gradient from 6% to 75% of Buffer B. The $\Delta 0:\Delta 0$ dimer eluted out at approximately 20–25% concentration of Buffer B. The $\Delta 0:\Delta 2$ and the $\Delta 2:\Delta 2$ dimers eluted out at approximately 30–35% concentration of Buffer B.

Gel-Filtration Chromatography

Separate concentrated hydroxyapatite pools containing the Δ0:Δ0 IL-10 dimer (up to ~20 mg/ml) were loaded onto either a SEPHACRYL® S-200 HR or SEPHACRYL® S-100 HR column (2.6×85 cm) equilibrated and eluted with Buffer C which was comprised of 20 mM Tris-Cl, 150 mM NaCl, pH 8.1. The sample loading volume was less than 4% of the bed volume and the flow rate was 0.1 cm/min. Peak fractions were pooled and stored at −20° C.

Gel filtration chromatography in either SEPHACRYL® S-200 HR or SEPHACRYL® S-100 HR revealed that hIL-10 displayed a molecular weight consistent with a dimeric form. The Δ0:Δ0 dimer was the predominant form for all protein concentrations loaded (0.2–20 mg/ml of bed volume). Small amounts (<5%) of hIL-10 monomer were occasionally seen as a trailing shoulder on a $A_{280}$ profile, and these fractions were excluded from the pool.

The overall purification procedure yielded approximately 1.1 mg of at least 98% pure Δ0:Δ0 human IL-10 per liter of cell culture medium. Purity was determined by sodium dodecyl sulfate-polyacrylamide gel electrophoresis (SDS-PAGE), Laemmli, U. K., *Nature*, 227: 680 (1970). In addition, HPLC chromatography with either reversed-phase ($C_4$) or with size exclusion ZORBEX® 250 showed only a single peak. The performance of each of the purification steps is shown in the following Table, in which results are an average from three purification runs of approximately 175 liters each of CHO cell supernatant (containing 5% Nu-Serum V).

TABLE 1

Purification of CHO hIL-10

| Step | Absorbance ($A_{280}$ units) | Total Proteins (mg) | hIL-10[a] (mg) | Yield[a] (%) | Purity[b] (%) |
|---|---|---|---|---|---|
| cell culture | 55,000 | 57,000 | 600 | 100 | 1.1 |
| S-Sepharose | 680 | 890 | 430 | 72 | 48 |
| Q-Sepharose | 190 | 360 | 290 | 48 | 81 |
| Hydroxyapatite | 130 | 200 | 210 | 35 | 92 |
| Sephacryl S-200 | 73 | 180 | 200 | 33 | 98 |

[a]Concentration and yield of hIL-10 was based on an ELISA assay.
[b]Purity was determined as mg hIL-10 (as determined by ELISA)/mg total protein (as determined by the Bradford Assay supra) × 100 for the cell culture concentrate, S-Sepharose pool, and Q-Sepharose pool. Purity was determined from SDS-PAGE by comparison of band intensity at varying protein amounts for the hydroxyapatite pool and the Sephacryl S-200 pool. In this technique known amount of the sample ranging from 0.005–25 µg were run in different lanes of an SDS-PAGE gel. The relative amount of contaminants seen at high loading were determine by comparison with the band intensity of IL-10 seen at low loadings.

EXAMPLE 2

Purification of Human IL-10 from *E. coli*

*Escherichia coli* (*E. coli*) was transformed with an expression plasmid containing a gene encoding and expressing recombinant human Interleukin-10 (rhuIL-10). The plasmid carried the strong hybrid tac promoter for transcription of the rhuIL-10 [Zurawski, S. M. et al., *J. Immunol.* 137:3354-3360 (1986)]. The lpp 3' coding and non-coding regions including the transcription terminator, lie downstream of the rhuIL-10 coding region. Derived from pINIIIompA, this region of the lpp gene is believed to lend stability to mRNA upstream of it [Ghrayeb, J. et al., *EMBO J.*, 3:2437-2442 (1984)]. The plasma carries a thermoinducible origin of replication, derived from pVU208, a copy control mutant derived from pCloDF13 [Hakkart, M. J. J. et al. 183:326-332 (1981)]. At elevated temperatures, e.g., 42° C., plasmid copy number for a different plasmid carrying this origin of replication has been reported to increase from about 30 copies per chromosomal equivalent to several hundred [Andreoli, P. M. et al., *J. Bacteriol.* 135:612-621 (1978)]. The plasmid carries the tetracycline resistance gene from pBR322 for plasmid maintenance [Sutdiffe, J. G., *C.S.H. Symp. Quant. Biol.* 43:77-90 (1978)]. The expression construct results in the rhIL-10 being produced intracellularly as insoluble inclusion bodies. The transformed *E. coli* were plated on agar containing 20 g/L tryptone, 10 g/L yeast extract, 5 g/L NaCl and 10 mg/L tetracycline. A single, well isolated colony was randomly picked from the agar plate and restreaked on a second agar plate.

A master cell bank was then prepared by suspending two colonies from the freshly restreaked agar plate in 1 ml of LYM-1 medium containing 30 g/L casamino acids, 20 g/L yeast extract, 5 g/L $KPO_4$ [monobasic], 20 g/L glycerol, 1 g/L $MgSO_4$, pH 7. This was then used to inoculate 100 ml of LYM-1 broth containing 10 mg/L tetracycline [LYM-1/Tc10] in a 300 ml baffled flask, which was then incubated at 30° C. and shook using a rotary shaker at 300 rotations per minute (RPM) until the cell density reached $Klett_{540}$ of ~400 (early log phase). This culture was then mixed 1:1 with 40% glycerol (v/v), yielding a final glycerol concentration of 20%. One ml aliquots were then dispensed into prelabeled cryovials quickly frozen under liquid nitrogen, and stored in a freezer set at −80° C. prior to use. A working cell bank was then prepared by thawing one vial of the master cell bank in air at room temperature which was then inoculated into 100 ml of LYM-1/Tc10 medium in a 300 ml baffled flask, which was then incubated at 30° C. and shook using a rotary shaker at 300 RPM until the culture reached Klett of ~400 (early log). This culture was then mixed 1:1 with 40% glycerol. One ml aliquots were then dispensed into prelabeled cryovials, quickly frozen under liquid nitrogen, and stored in a freezer set at −80° C.

A 1.5 ml frozen vial of the working stock was thawed at room temperature. Approximately 0.5 ml of the working stock was transferred into a 2000 ml flask which contained 500 ml of LYM-1/Tc10 medium. The tetracycline was added just before inoculation. The flask 5 was placed on a rotary shaker and shook at 300 RPM at 30° C. After 6.5–7 hrs a sample was removed from the flask for $Klett_{540}$ determination. The culture had a $Klett_{540}$ of 200–300. A 1000 liter fermentor containing 800 liters of LYM-3/Tc10 medium was then inoculated with the contents of the 2000 ml flask. LYM-3/Tc10 medium is comprised of 30 g/l Casein Digest-HyCase P (Sheffield), 20 g/l Yeast Extract-Type D (Bio Springer), 15 g/l Potassium Phosphate-Monobasic (Monsanto), 0.5 ml/l of a 30% suspension of SAG-471® (Union Carbide), 20 g/l Glycerin 99.7% (Univar), 1 g/l Magnesium Sulfate-7 $H_2O$ (PQ), 10 mg/l tetracycline (Sigma), 2 ml/l Iron Citrate Stock Solution comprised of 2 ml/l sulfuric acid, 15 g/l Sodium Citrate, 13.5 g/l Ferric Chloride Hexahydrate. The pH of the medium was adjusted to about 7 with a solution of 50% NaOH and a solution of 75% $H_3PO_4$. The temperature of the inoculated medium within the fermentor was maintained at 30° C.±0.5° C. until 1000±100 $Klett_{540}$ was reached and then the temperature was elevated to 38° C.±0.5° C. for 14 hours. The dissolved oxygen concentration in the fermentor was maintained at a level greater than 40% of saturation by agitation.

The fermentation was harvested 14 hours after the temperature was elevated to 38° C. by lowering the agitation, and chilling the medium to 5° C.–15° C. The batch was centrifuged using a contained CSA-16 continuously desludging centrifuge at a feed flowrate of approximately 5–10 liters per minute (lpm). The flowrate was adjusted in order to obtain a clear centrate. One full desludge and one partial desludge (with bowl time set at 0.95 sec) was used to recover 800 liter of fermentation. A 40±2kg cell pellet was recovered in the centrifugation step.

The 40 kg cell pellet recovered in the centrifugation step was homogenized using a Gaulin M12 homogenizer at an operating pressure of 7000–8000 psi for the equivalent of 6 passes. This was accomplished by recirculating the batch from a hold tank through the homogenizer and a glycol-cooled heat exchanger and back to the hold tank at a flowrate of 10 lpm for approximately 140 min. After the 140 min homogenization, a sample of the homogenate was withdrawn and examined under a phase contrast microscope. This was done in order to assess cell breakage. If greater than 95% breakage, as estimated by microscopic evaluation, is not observed, then homogenization should be continued.

The homogenized cells were inactivated by mixing the homogenate with an equal volume of 4M Guanidine Buffer comprised of 6.05 g/l TRIZMA-BASE® (Tris [hydroxymethyl]aminomethane) (Sigma), 1.90 g/l disodium EDTA dihydrate (Sigma), 58.4 g/l NaCl USP (Mallinckrodt), and 382 g/l Guanidine HCl (Sigma). The resuspension was held for 30 min. at 10°–15° C. under slow agitation. The inactivated resuspension was then centrifuged in a Sharples AS26SP centrifuge at a flowrate of 500 ml per minute and a centrifuge speed of 17000 rpm. A pellet containing inclusion bodies recovered in this step was frozen at −10° C. Inclusion bodies are aggregates that contain various *E. coli* host proteins, nucleic acids and other cellular debris, in addition to h-IL-10.

Unfolding IL-10

The inclusion body pellet which had been stored at −10° C. was thawed for three days at 2°–10° C. in a cold room. The pellet was broken up and added into 20 liters of unfolding buffer. The unfolding buffer was comprised of 50 mM TRIZMA® (Tris[hydroxymethyl]aminomethane) (Sigma), 7M guanidine HCl, and 4 mM dithiothreitol (DTT), pH 8.5. The inclusion body pellet was vigorously agitated with a polytron homogenizer to form a fine suspension. This suspension was then allowed to further solubilize by slow agitation for approximately 3 hours at 2°–10° C.

Refolding IL-10

The soluble protein solution was then diluted approximately twenty five fold into a refolding buffer. The refolding buffer was comprised of 50 mM TRIZMA®, 0.12M Guanidine HCl, 0.05 mM Glutathione (reduced), pH 8.5. The diluted refolding solution was immediately clarified by filtration; an oxidized glutathione solution was then added to a 0.45 mM final concentration and refolding continued for 10–24 hours.

Concentration/Diafiltration

At the end of the refolding step, the solution was then clarified by filtration using a 0.45 μm filter prior to ultrafiltration. Additionally, a filter may be placed in line to the ultrafilter to ensure clarity during ultra filtration. The solution containing the refolded IL-10 was then concentrated approximately 10 fold. This was done with the ultrafiltration system Millipore PELLICON® ultrafilter with 10,000 nominal molecular weight PLGC membranes. The concentrate was then diafiltered to reduce the concentrate conductivity to approximately 6 mS. The diafiltration buffer was comprised of pH 8.5, 20 mM TRIS, 20 mM NaCl.

Cation Exchange Chromatography

The concentrated solution containing the refolded h-IL-10 was adjusted to 20 mM BIS-TRIS, pH 6.5 by the addition of 1M BIS-TRIS and 4N HCl. The solution was then clarified by filtration. The clarified feed solution containing approximately 1.2 mg of protein/ml was then applied to a 12 liter (12 cm×36 cm diameter) S-SEPHAROSE® Fast Flow suffonate column (Pharmacia, Piscataway, N.J.) at a rate of 1 cm/min. The column had been pre-equilibrated with ten bed volumes of a pH 6.5, 20 mM BIS-TRIS, 0.065M NaCl buffer, pH 6.5 at a rate of 1 cm/min. Elution was performed with a 20 column volume gradient in the range of 0.065–0.4M NaCl, 20 mM BIS-TRIS, pH 6.5 buffer at a rate of 0.5 cm/min. The h-IL-10 peak fractions of the elution profile were determined by $A_{280}$ and verified by typical pH and conductivity ranges. The fractions containing the h-IL-10 eluted at 11–18 mS, 100–170 mM NaCl and were pooled together for further processing.

Anion Exchange Chromatography

The pooled fractions from the cation exchange chromatography process containing the h-IL-10 were concentrated to 0.5 column volumes with an ultrafiltration system Millipore PELLICON® ultrafilter with 10,000 n.mol.wt. PLGC membranes. The concentrate was then diafiltered to approximately 1.5 mS using a 10 mM TRIS buffer pH 8.7. The pH of the diafiltered concentrate was adjusted to pH 8.7 with HCl or NaOH. The solution containing approximately 13 mg/ml of protein was applied to a 6 liter (18 cm diameter× 23.5 cm) quaternary ammonium column Q-SEPHAROSE® Fast Flow (Pharmacia) at a flow rate of 0.5 cm/min. pre-equilibrated with 10 mM TRIS, 8 mM NaCl, pH 8.7 buffer. The h-IL-10 has a differential attraction to the resin versus the impurities contained within the fractions and was separated on the isocratic elution and collected in the column effluent with 10 mM TRIS, 8 mM NaCl, pH 8.7 buffer. The acetylated homodimers and acetylated heterodimers adsorbed more strongly to the resin, and thus were separated from the non-acetylated homodimers. The non-acetylated h-IL-10 peak fractions of the elution profile as determined by $A_{280}$ were pooled for further processing.

Hydroxyapatite Chromatography

The pool containing the h-IL-10 obtained from the anion exchange chromatography step was applied to a 4 liter (26 cm×14 cm diameter) hydroxyapatite column (e.g., Ceramic Hydroxyapatite, Biorad MACRO-PREP) pre-equilibrated with 20 mM TRIS, 20 mM NaCl, pH 7.4 buffer. The column wash was performed by decreasing the amount of 20 mM TRIS buffer from 100% to 95% and increasing the level of pH 7.4, 0.15M sodium phosphate buffer 0% to 5% for approximately 4 column volumes. The elution was performed by increasing the percent of phosphate buffer during a 17 bed volume elution gradient from 5% to 100%. The non-covalently bonded dimer eluted at 7–10 mS, while the covalently bonded dimer peaked at 12 mS. The h-IL-10 peak fractions as determined by $A_{280}$ were pooled for further processing.

Gel Filtration Chromatography

The pool from the hydroxyapatite process step containing the non-acetylated, non-covalently bonded IL-10 dimer was concentrated on an ultrafiltration system containing a 10,000 n. molecular weight membrane. The concentrate was applied to a gel filtration column which was a 14.8 liter (96 cm×14 cm diameter) SEPHACRYL® S-200 HR, pre-equilibrated with 10 mM TRIS buffer, pH 7.4. The column was eluted with a pH 7.4, 10 mM TRIS buffer. The h-IL-10 peak fractions of the elution profile as determined by $A_{280}$ were pooled for further processing. The gel filtration pool was filtered through a 0.2 μm filter. The filtrate, the final purified bulk drug, was stored at −20° C.

Gel filtration chromatography in either SEPHACRYL® S-200 HR or SEPHACRYL® S-100 HR revealed that hIL-10 displayed a molecular weight consistent with a dimeric form. The non-acetylated, non-covalently bonded dimer was the predominant form for all protein concentrations loaded (0.2–20 mg/ml of bed volume). Small amounts (<5%) of hIL-10 monomer were occasionally seen as a trailing shoulder on the $A_{280}$ profile, and these fractions were excluded from the pool.

The performance of each of the purification steps is shown in the following Table 2.

TABLE 2

Purification of hIL-10 Expressed by E. coli

| Step | Absorbance ($A_{280}$ units) | Total Proteins (mg) | hIL-10[a] (mg) | Yield[a] (%) | Purity[a] (%) |
|---|---|---|---|---|---|
| Refolding[b] | 183,000 | 161,000 | 44,800 | 100 | 45 |
| S-Sepharose | 21,700 | 42,000 | 28,900 | 65 | 81 |
| Q-Sepharose | 6,860 | 18,900 | 17,300 | 39 | 99 |
| Hydroxyapatite | 5,670 | 16,500 | 13,700 | 31 | 99 |
| Sephacryl S-200 | 4,950 | 14,400 | 12,000 | 27 | 99 |

[a]Concentration, yield and purity of hIL-10 was based on Reverse Phase HPLC analysis.
[b]After concentration, diafiltration, and pH adjustment.

EXAMPLE 3

Hydrophobic Interaction Chromatography of Refolded Human IL-10

As an alternative to diafiltration of the refolded IL-10 the following procedure can be used to remove the refolding and denaturing buffers. Inclusion bodies containing human IL-10 which had been expressed in *E. coli* were resuspended in a 10:1 (v/w) ratio of unfolding buffer to inclusion bodies. The unfolding buffer was comprised of 6M Guanidine Hydrochloride (GdnHCl), 4 mM dithiothreitol (DTT), 50 mM Tris pH 8.5, 1 mM ethylene diamine tetraacetic acid (EDTA), and 1 mM phenylmethylsulfoxyl fluoride (PMSF). The buffer containing the inclusion bodies was incubated with stirring for three hours at 4° C. producing unfolded, denatured human IL-10.

The unfolded denatured IL-10 was diluted 100 fold into a refolding buffer containing 50 mM Tris pH 8.5, 1 mM EDTA, 0.5M final concentration of GdnHCl, 4.17 mM reduced glutathione, 0.83 mM oxidized glutathione, 2 mM benzamidine and incubated for 17 hours at 4° C.

After refolding, the mixture was filtered through a 0.45 μm filter, brought to 25% ammonium sulfate concentration and filtered again. The filtrate was applied to a Butyl-Toyopearl 650M Hydrophobic Interaction (TosoHaas) column (pre-equilibrated into 25% ammonium sulfate, 20 mM Tris pH 8.5), at a ratio of 0.25 to 0.5 grams of inclusion bodies per ml of resin at a linear flow rate of 1 cm/min. In this step, the IL-10 was bound to the column while many of the protein and most of the non-protein contaminants such as the refolding process reagents such as glutathione and GdnHCl, low molecular weight contaminants, fragments of *E. coli* cell components etc. which are characteristic of refolding mixtures passed through the column. The bound human IL-10 was then eluted isocratically with 20 mM Tris pH 8.5, 20–50 mM NaCl. Twenty one-bed volume fractions were collected. The human IL-10 began to elute two bed volumes into the isocratic gradient. Generally, fractions 2–15 were pooled. The hydrophobic interaction pool can then be further processed for further purification.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention, which is only to be limited by the claims.

What is claimed is:

1. A method for purifying bacterially expressed human Interleukin-10 (IL-10) contained within a solution comprising:

(a) applying a solution containing IL-10 to a cation exchange chromatography column thereby obtaining fractions containing IL-10;

(b) applying the IL-10-containing fractions from step (a) to an anion exchange chromatography column thereby obtaining fractions containing IL-10;

(c) applying the IL-10-containing fractions from step (b) to a hydroxyapatite chromatography chromatography thereby obtaining fractions containing a single isolated dimer of IL-10.

2. The method of claim 1 wherein the cation exchange chromatography column from step (a) is comprised of sulfonate exchange groups attached to a support matrix.

3. The method of claim 2 wherein the support matrix is agarose.

4. The method of claim 1 wherein the anion exchange chromatography column is comprised of quaternary amino ethyl exchange groups attached to a support matrix.

5. The method of claim 4 wherein the support matrix is agarose.

6. The method of claim 1 further comprising applying the IL-10-containing fractions obtained from step (c) of claim 1 to a gel filtration chromatography column to obtain dimeric IL-10 substantially free of high and low molecular weight impurities.

7. The method of claim 6 wherein the material in the gel filtration chromatography column has a fractionation range of from 1 to 600 kDa.

8. The method of claim 1 wherein prior to step (a) the bacterially expressed human IL-10 is extracted from bacteria in inclusion bodies, denatured and refolded into biologically active human IL-10.

9. A method for separating non-acetylated homodimers of Interleukin-10 (IL-10) from acetylated IL-10 homodimers and from acetylated IL-10 heterodimers contained within a solution comprising:

applying the solution to an anion exchange chromatography column under conditions in which the non-acetylated homodimers are separated from the acetylated homodimers and from the acetylated heterodimers.

* * * * *